United States Patent
Taira et al.

(10) Patent No.: US 11,448,634 B2
(45) Date of Patent: Sep. 20, 2022

(54) ANALYSIS APPARATUS, STRATUM AGE ESTIMATION APPARATUS, ANALYSIS METHOD, STRATUM AGE ESTIMATION METHOD, AND PROGRAM

(71) Applicants: NEC CORPORATION, Tokyo (JP); JAPAN AGENCY FOR MARINE-EARTH SCIENCE AND TECHNOLOGY, Yokosuka (JP);
(Continued)

(72) Inventors: Yousuke Taira, Tokyo (JP); Naoki Kuwamori, Tokyo (JP); Tatsuhiko Hoshino, Yokosuka (JP); Jonaotaro Onodera, Yokosuka (JP); Tatsuhiko Yamaguchi, Kochi (JP); Kyoko Tomioka, Kochi (JP); Takuya Itaki, Tsukuba (JP)

(73) Assignees: NEC CORPORATION, Tokyo (JP); JAPAN AGENCY FOR MARINE-EARTH SCIENCE AND TECHNOLOGY, Kanagawa (JP);
(Continued)

( * ) Notice: Subject to any disclaimer, the term of this patent is extended or adjusted under 35 U.S.C. 154(b) by 359 days.

(21) Appl. No.: 16/611,263

(22) PCT Filed: May 10, 2018

(86) PCT No.: PCT/JP2018/018172
§ 371 (c)(1),
(2) Date: Nov. 6, 2019

(87) PCT Pub. No.: WO2018/207885
PCT Pub. Date: Nov. 15, 2018

(65) Prior Publication Data
US 2020/0166497 A1    May 28, 2020

(30) Foreign Application Priority Data

May 10, 2017 (JP) .............................. JP2017-094086

(51) Int. Cl.
*G06K 9/00* (2022.01)
*G01N 33/24* (2006.01)
(Continued)

(52) U.S. Cl.
CPC ............. *G01N 33/24* (2013.01); *G01N 21/84* (2013.01); *G06V 20/695* (2022.01); *G06V 20/698* (2022.01); *G01N 2201/125* (2013.01)

(58) Field of Classification Search
CPC .... C12Q 1/04; G01N 21/84; G01N 2201/125; G01N 33/24; G01V 8/02; G06V 20/695; G06V 20/698
See application file for complete search history.

(56) References Cited

U.S. PATENT DOCUMENTS 10,502,863 B2 * 12/2019 Mosse .................. G01V 99/005
10,724,348 B2 *  7/2020 Chauveau ............ G01V 99/005
(Continued)

FOREIGN PATENT DOCUMENTS

CN      101477630 A      7/2009
CN      104081001 A      10/2014
(Continued)

OTHER PUBLICATIONS

Communication dated Jan. 18, 2021 from The Patent Office of the P.R. of China in Application No. 2018800309295.
(Continued)

*Primary Examiner* — Avinash Yentrapati
(74) *Attorney, Agent, or Firm* — Sughrue Mion, PLLC

(57) ABSTRACT

An analysis apparatus (100) includes an image acquisition unit (110) and an analysis unit (120). The image acquisition
(Continued)

unit (110) acquires image data of a microfossil in a sample collected from a stratum. The analysis unit (120) analyzes the image data acquired by the image acquisition unit (110) using a machine learning result to analyze a taxon or kind of the microfossil in the image data.

11 Claims, 13 Drawing Sheets

(51) Int. Cl.
*G01N 21/84* (2006.01)
*G06V 20/69* (2022.01)

(71) Applicants: NATIONAL UNIVERSITY CORPORATION KOCHI UNIVERSITY, Kochi (JP); NATIONAL INSTITUTE OF ADVANCED INDUSTRIAL SCIENCE AND TECHNOLOGY, Tokyo (JP)

(73) Assignees: NATIONAL UNIVERSITY CORPORATION KOCHI UNIVERSITY, Kochi (JP); National Institute of Advanced Industrial Science and Technology, Tokyo (JP)

(56) References Cited

U.S. PATENT DOCUMENTS

| | | | |
|---|---|---|---|
| 2005/0002560 A1 | 1/2005 | Yamamoto et al. | |
| 2014/0377873 A1* | 12/2014 | Hay | E21B 49/081 436/29 |
| 2015/0302255 A1 | 10/2015 | Gershtein et al. | |
| 2019/0114352 A1* | 4/2019 | Sung | G06F 16/211 |
| 2020/0326455 A1* | 10/2020 | Tiedemann | G01V 99/005 |

FOREIGN PATENT DOCUMENTS

| | | |
|---|---|---|
| CN | 104199124 A | 12/2014 |
| CN | 104205128 A | 12/2014 |
| CN | 104331712 A | 2/2015 |
| CN | 105608447 A | 5/2016 |
| CN | 106327451 A | 1/2017 |
| EA | 010117 B1 | 6/2008 |
| FR | 3 018 354 A1 | 9/2015 |
| JP | 2004-354250 A | 12/2004 |
| JP | 2015-512075 A | 4/2015 |
| RU | 1 331 289 A1 | 4/1995 |
| WO | 2013112591 A1 | 8/2013 |
| WO | 2015/132531 A1 | 9/2015 |
| WO | WO-2015132531 A1 * | 9/2015 ............. G01N 21/23 |

OTHER PUBLICATIONS

Louise Ann Apostol et al., "RADSS: A Radiolarian Classifier Using Support Vector Machines", 2016, 7th International Conference on Information, Intelligence, Systems & Applications (IISA), IEEE, pp. 1-6 (7 pages).

Ma Qiangfen et al., "Taxonomy and Biostratigraphy of the Middle Permian Radiolarian Fauna From the Gufeng Formation in Luojiaba, West Hubei Province", Acta Micropalacontologica Sinica, 2012, vol. 29, Issue 4, pp. 402-415 (14 pages total).

Extended European Search Report dated Jan. 20, 2021 from the European Patent Office in Application No. 18799136.9.

Communication dated Aug. 4, 2020, from the Japanese Patent Office in Application No. 2019-517700.

Communication dated Sep. 28, 2021 from the China National Intellectual Property Administration in Chinese Application No. 201880030929.5.

Kuang Shenai et al., "A Preliminary Test of Using Digital Image Processing In Micropalaeontology", Acta Geologica Sinica, 1985, Issue 4, pp. 356-362 (9 pages total).

Jing Xia et al., "Conodont Digital Image Acquisition and the Method of Image Enhancement", Acta Palaeontologica Sinica, 2014, vol. 53, No. 3, pp. 392-399 (8 pages total).

Decision to Grant a Patent dated Jan. 5, 2021 from the Japanese Patent Office in JP application No. 2019-517700.

Office Action dated Jun. 30, 2020 in Russian Application No. 2019139664.

Beaufort et al., "Automatic recognition of coccoliths by dynamical neural networks", Marine Micropaleontology, 2004, vol. 51, pp. 57-73 (17 pages total).

Tanimura Yoshihiro et al., "Microfossils: The world of plankton fossils seen with a microscope", National Science Museum Sosho, Tokai University Press, Aug. 2012, pp. 86-87, 282-288 and 308-309.

Kiyoshi Wadatsumi et al., "Information Geoscience in the Present and the Future", Geological data processing, Oct. 31, 1986, vol. 11, pp. 1-6.

Masato Watanabe et al., "Diatom biostratigraphy of the Kinone and the Amatsu Formaition, Boso Peninsula, Japan.", Annual Meeting of the Geological Society of Japan, the 102th annual meeting, Mar. 20, 1995, p. 137.

International Search Report for PCT/JP2018/018277 dated Jul. 31, 2018 [PCT/ISA/210].

Written Opinion of the International Searching Authority for PCT/JP2018/018277 dated Jul. 18, 2018 [PCT/ISA/237].

Huang Bin et al., "Object recognition algorithm based on deep convolution neural networks", Journal of Computer Applications, 2016, vol. 36, No. 12, pp. 3333-3346 (9 pages), ISSN 1001-9081.

Communication dated Mar. 18, 2022, issued in Chinese Application No. 201880030929.5.

* cited by examiner

FIG. 6

| KIND OF MICROFOSSIL | PREPROCESSING | PARAMETER |
|---|---|---|
| COCCOLITHOPHORE | ADJUST "BRIGHTNESS", "EDGE", AND "CONTRAST" | ADJUSTMENT PARAMETER P1 |
| DIATOM | ADJUST "BRIGHTNESS" AND "CONTRAST" | ADJUSTMENT PARAMETER P2 |
| ⋮ | ⋮ | ⋮ |

FIG. 7

(a) ANALYSIS RESULT OF IMAGE DATA

|  | SIZES (DIAMETER) | CERTAINTY FACTOR FOR ALGA A | CERTAINTY FACTOR FOR ALGA B | CERTAINTY FACTOR FOR ALGA C | CERTAINTY FACTOR FOR ALGA D |
|---|---|---|---|---|---|
| IMAGE 1 | 10 | 05% | 20% | 10% | 50% |
| IMAGE 2 | 11 | 01% | 25% | 80% | 30% |
| IMAGE 3 | 14 | 03% | 32% | 10% | 75% |
| IMAGE 4 | 12 | 02% | 10% | 10% | 50% |
| IMAGE 5 | 13 | 10% | 40% | 10% | 30% |
| IMAGE 6 | 09 | 30% | 50% | 10% | 20% |
| IMAGE 7 | 10 | 04% | 10% | 70% | 30% |

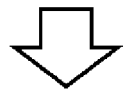

(b) DISTRIBUTION OF MICROFOSSIL IN SAMPLE

| ALGA A | ALGA B | ALGA C | ALGA D |
|---|---|---|---|
| 05% | 10% | 35% | 50% |

↕ COMPARE (c) STANDARD DISTRIBUTION FOR EACH AGE

|  | ALGA A | ALGA B | ALGA C | ALGA D | ... |
|---|---|---|---|---|---|
| AGE 1 | 90% | 00% | 00% | 00% |  |
| AGE 2 | 10% | 50% | 10% | 00% |  |
| AGE 3 | 01% | 10% | 40% | 40% |  |
| AGE 4 | 00% | 20% | 10% | 50% |  |
| AGE 5 | 00% | 10% | 10% | 80% |  |
| ⋮ | ⋮ | ⋮ | ⋮ | ⋮ |  |

FIG. 8

|  | ALGA A | ALGA B | ALGA C | ALGA D |
|---|---|---|---|---|
| NUMBER OF PIECE OF IMAGE DATA OF "CERTAINTY FACTOR: HIGH" | 40 | 5 | 0 | 0 |
| NUMBER OF PIECE OF IMAGE DATA OF "CERTAINTY FACTOR: MEDIUM" | 60 | 60 | 80 | 20 |
| NUMBER OF PIECE OF IMAGE DATA OF "CERTAINTY FACTOR: LOW" | 0 | 35 | 20 | 80 |

ANALYSIS APPARATUS, STRATUM AGE ESTIMATION APPARATUS, ANALYSIS METHOD, STRATUM AGE ESTIMATION METHOD, AND PROGRAM

CROSS REFERENCE TO RELATED APPLICATIONS

This application is a National Stage of International Application No. PCT/JP2018/018172 filed May 10, 2018, claiming priority based on Japanese Patent Application No. 2017-094086, filed May 10, 2017, the disclosures of which are incorporated herein in their entirety by reference.

TECHNICAL FIELD

The present invention relates to a technique of assisting a study of a stratum age based on a microfossil existing in a collected sample.

BACKGROUND ART

A study is performed in which an expert estimates an age of a stratum on the basis of a microfossil (zooplankton and algal fossils) existing in a sample collected from the stratum. The expert estimates the age of the stratum on the basis of a taxon of the microfossil existing in the sample, for example, with reference to a table or the like indicating an existence range of the taxon (classification unit of organisms such as kingdom, phylum, class, order, family, genus, and species) of the microfossil as disclosed in Non-Patent Document 1 below.

RELATED DOCUMENT

Non-Patent Document

[Non-Patent Document 1] Tanimura Yoshihiro and Tuji Akihiro, "Bikaseki: Kembikyo de miru purankuton kaseki no sekai (Microfossils: The world of plankton fossils seen with a microscope)", National Science Museum Sosho, Tokai University Press, August 2012, p. 86 to 87, 282 to 288, and 308 to 309

SUMMARY OF THE INVENTION

Technical Problem

It is of a significant academic or industrial benefit when an age of a stratum can be analyzed accurately. However, there are only a limited number of experts who can accurately estimate the age of the stratum on the basis of a microfossil included in the stratum, and it is extremely difficult for an inexperienced person to estimate the age of the stratum with the same accuracy as the expert.

The present invention is made in view of the above problems. One of the objects of the present invention is to provide a technique capable of accurately estimating an age of a stratum on the basis of a microfossil.

Solution to Problem

According to the present invention, there is provided an analysis apparatus including an image acquisition unit that acquires image data of a microfossil in a sample collected from a stratum, and an analysis unit that analyzes the image data using a machine learning result to analyze a taxon or kind of the microfossil in the image data.

According to the present invention, there is provided a stratum age estimation apparatus including an analysis result acquisition unit that acquires an analysis result of a taxon or kind of a microfossil in a sample collected from a stratum, and an age estimation unit that estimates and outputs an age of the stratum from which the sample is collected, using the analysis result.

According to the present invention, there is provided an analysis method executed by a computer. The analysis method includes acquiring, by the computer, image data of a sample collected from a stratum, and analyzing, by the computer, the image data using a machine learning result to analyze a taxon or kind of the microfossil in the image data.

According to the present invention, there is provided a stratum age estimation method executed by a computer. The stratum age estimation method includes acquiring, by the computer, an analysis result of a taxon or kind of a microfossil in a sample collected from a stratum, and estimating and outputting, by the computer, a stratum age of the sample using the analysis result.

According to the present invention, there is provided a program causing a computer to function as an image acquisition unit that acquires image data of a sample collected from a stratum, and an analysis unit that analyzes the image data using a machine learning result to analyze a taxon or kind of the microfossil in the image data.

According to the present invention, there is provided a program causing a computer to function as an analysis result acquisition unit that acquires an analysis result of a taxon or kind of a microfossil in a sample collected from a stratum and an age estimation unit that estimates and outputs a stratum age of the sample using the analysis result.

Advantageous Effects of Invention

According to the present invention, it is possible to accurately estimate the age of the stratum on the basis of the microfossil.

BRIEF DESCRIPTION OF THE DRAWINGS

The objects described above, and other objects, features and advantages will become more apparent from preferred example embodiments described below and the following drawings accompanying the example embodiments.

FIG. 6 is a diagram illustrating information defining preprocessing corresponding to a kind of the microfossil to be analyzed.

FIG. 7 is diagrams for illustratively describing a flow in which an age estimation unit estimates an age of a stratum for each kind of the microfossil.

FIG. 8 is a diagram showing an example of a result of classifying a final analysis result of each piece of image data on the basis of a certainty factor.

DESCRIPTION OF EMBODIMENTS

Figure 1:
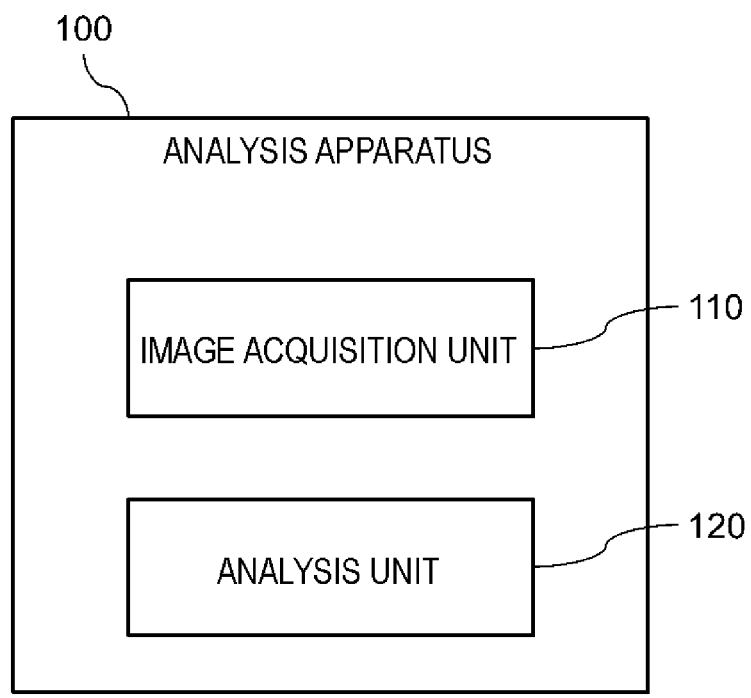
FIG. 1 is a block diagram conceptually showing a functional configuration of an analysis apparatus according to a first example embodiment.

[Outline of Stratum Age Estimation Method in the Related Art]

Before describing a configuration of the present invention, a method of estimating a stratum age using a microfossil in the related art will be outlined. In the method in the related art, a target stratum is first excavated by using a drilling apparatus such as a drill pipe to collect a sample of the stratum. Then, a preparation is created on the basis of the sample collected from the stratum in order to observe in detail the microfossil which is a clue to estimate the age of the stratum to be studied. A pretreatment is performed for each of target microfossils (for example, coccolithophore, diatom, radiolaria, and foraminifera used as so-called index fossils) to create the preparation. An expert sets the preparation on a microscope to discriminate a taxon (classification group) of the microfossil existing in the sample. Then, the expert estimates an approximate age of the stratum from which the sample is collected with reference to the discriminated taxon of the microfossil and, for example, the existence period of each taxon of the microfossil disclosed in Non-Patent Document 1. In this case, a combination of taxa of the microfossil, a size of the microfossil, and the like are significant clues for estimating the age. Then, a final stratum age is discussed and decided on the basis of the age estimated for each kind of the microfossil (age estimated from an observation result of coccolithophore, age estimated from an observation result diatom, or the like).

As described above, there are only a limited number of people who can accurately estimate the age using the index fossil. In the present invention described below, it is possible for even an inexperienced person to accurately estimate the age of the microfossil. It is possible to accurately estimate the age of the stratum using the estimation result of the age of the microfossil. Accordingly, it is possible to solve the problem such as a shortage of experts as well.

Hereinafter, example embodiments of the present invention will be described with reference to the drawings. It should be noted that the same reference numeral is assigned to the same component for all the drawings, and the description thereof will not be repeated. Further, each block represents a configuration of functional units instead of a configuration of hardware units in each block diagram, unless otherwise described.

First Example Embodiment

[Functional Configuration]

FIG. 1 is a block diagram conceptually showing the functional configuration of an analysis apparatus 100 according to a first example embodiment. As shown in FIG. 1, the analysis apparatus 100 according to the present example embodiment includes an image acquisition unit 110 and an analysis unit 120.

The image acquisition unit 110 acquires image data of a microfossil existing in a sample collected from a stratum. This image data is generated by imaging a preparation created from the sample collected from the stratum in a microscope apparatus or the like. This preparation is created for each kind of the microfossils to be analyzed (for example, classification of coccolithophore, diatom, radiolaria, foraminifera, and the like).

The analysis unit 120 processes the image data acquired by the image acquisition unit 110 using a machine learning result to analyze the taxon or kind of the microfossil in the image data. This machine learning result is a model (for example, a neural network such as a convolutional neural network (CNN)) constructed with a past classification result (combination of image data of a microfossil and the classification of the microfossil) by an expert as training data, that is, a model constructed by learning knowledge of the expert.

[Hardware Configuration]

Each functional configuration unit of the analysis apparatus 100 may be formed by hardware (for example, a hard-wired electronic circuit) implementing each functional configuration unit, or a combination of hardware and software (for example, a combination of an electronic circuit and a program that controls the circuit). Hereinafter, a case where each functional configuration unit of the analysis apparatus 100 is formed by the combination of hardware and software will be further described.

Figure 2:
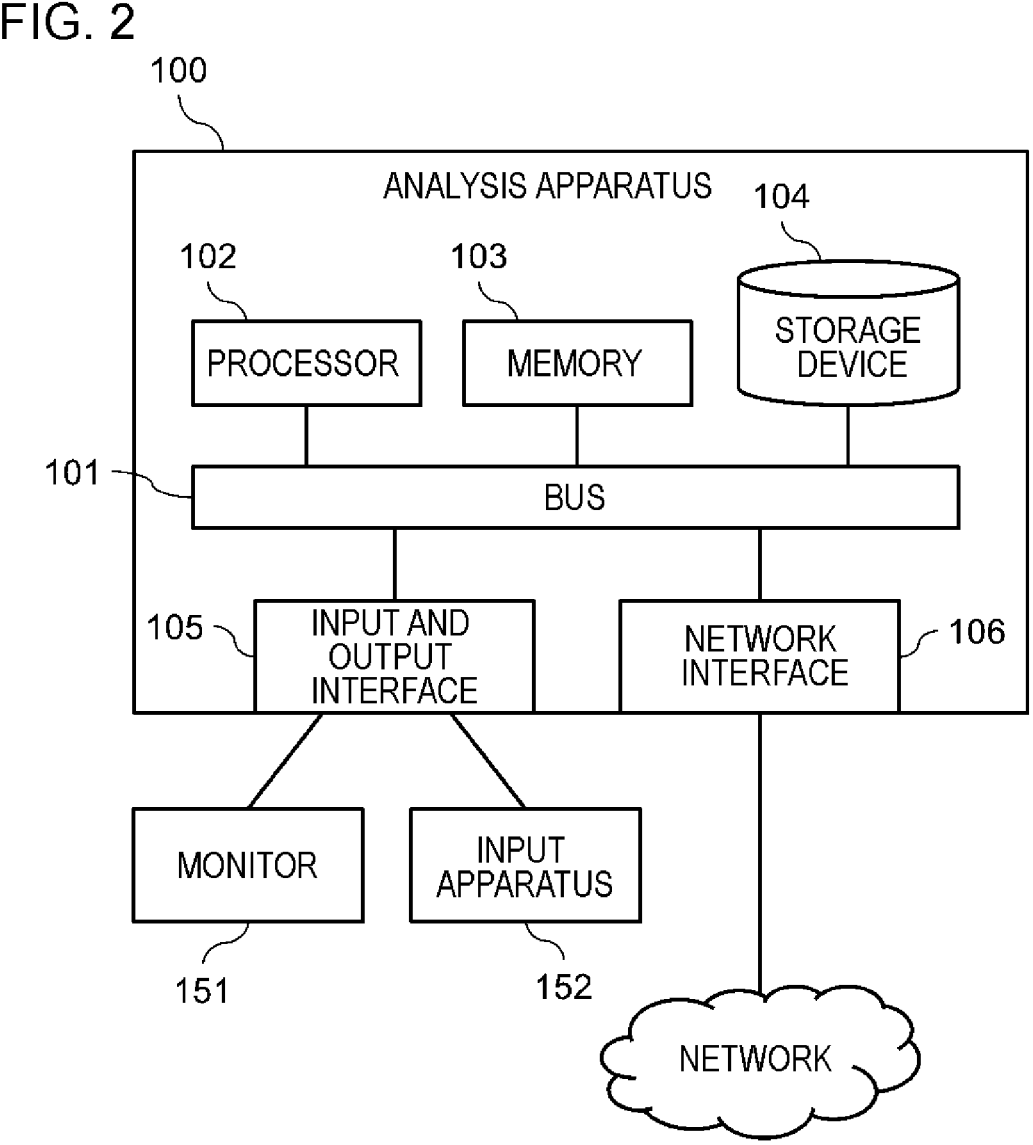
FIG. 2 is a diagram conceptually showing a hardware configuration of the analysis apparatus.

FIG. 2 is a diagram conceptually showing a hardware configuration of the analysis apparatus 100. As shown in FIG. 2, the analysis apparatus 100 includes a bus 101, a processor 102, a memory 103, a storage device 104, an input and output interface 105, and a network interface 106.

The bus 101 is a data transmission path for the processor 102, the memory 103, the storage device 104, the input and output interface 105, and the network interface 106 to mutually transmit and receive data. However, a method of connecting the processor 102, the memory 103, the storage device 104, the input and output interface 105, the network interface 106, and the like to one another is not limited to the bus connection.

The processor 102 is an arithmetic apparatus such as a central processing unit (CPU) or a graphics processing unit (GPU). The memory 103 is a main storage apparatus formed by using a random access memory (RAM), a read only memory (ROM), or the like. The storage device 104 is an auxiliary storage apparatus formed by using a hard disk drive (HDD), a solid state drive (SSD), a memory card, or the like.

The storage device 104 stores program modules implementing the respective functional configuration units (the image acquisition unit 110 and the analysis unit 120) of the analysis apparatus 100. The processor 102 reads each of the program modules into the memory 103 and executes each program module to realize a function corresponding to each program module.

The input and output interface 105 is an interface for connecting the analysis apparatus 100 to a monitor 151, an input apparatus 152, and the like. The monitor 151 is a device for display output such as a liquid crystal display (LCD) or a cathode ray tube (CRT) display. The input apparatus 152 is a device for input such as a keyboard or a mouse.

The network interface 106 is an interface for connecting the analysis apparatus 100 to a communication network such as a local area network (LAN) or a wide area network (WAN). As shown in FIG. 2, the analysis apparatus 100 can communicate with an external server apparatus (not shown) by being connected to the communication network through the network interface 106. It should be noted that a method of connecting to the communication network may be a wireless connection or a wired connection.

Operation Example

Figure 3:
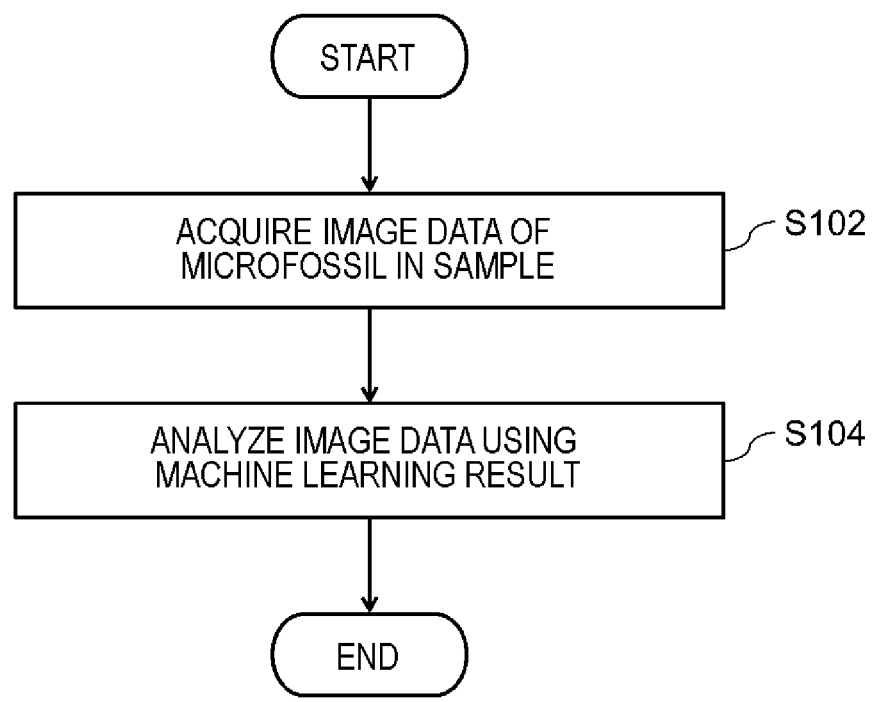
FIG. 3 is a flowchart illustrating an operation of the analysis apparatus according to the first example embodiment.

An operation of the analysis apparatus 100 in the present example embodiment will be illustrated in FIG. 3. FIG. 3 is a flowchart illustrating the operation of the analysis apparatus 100 according to the first example embodiment.

The image acquisition unit 110 acquires the image data of the microfossil in the sample from the microscope apparatus or the like in which the preparation created on the basis of the sample collected from the stratum is set (S102). The analysis unit 120 analyzes the image data of the microfossil acquired by the image acquisition unit 110 using the machine learning result such as CNN (S104). For example, the analysis unit 120 can input the image data of the microfossil acquired by the image acquisition unit 110 into the machine learning result and obtain an analysis result of the taxon of the microfossil in the image data as an output.

As described above, in the present example embodiment, it is possible to obtain the analysis result (discrimination result) of the taxon of the microfossil in the image data by processing the image data of the microfossil existing in the sample collected from the stratum using the machine learning result. Discriminating the taxon of the microfossil is an important part in estimating the stratum age using the microfossil and requires experience. In the present example embodiment, the image data of the microfossil is analyzed using the machine learning result constructed by learning the knowledge of the experienced expert. Therefore, it is possible for even an inexperienced person to accurately analyze the taxon of the microfossil. Further, it is possible for even an inexperienced person to accurately estimate the age of the stratum by collating this analysis result with the existence period of each microfossil disclosed in Non-Patent Document 1 and the like.

Second Example Embodiment

The present example embodiment has the same configuration as the first example embodiment except for the following points.

[Functional Configuration]

Figure 4:
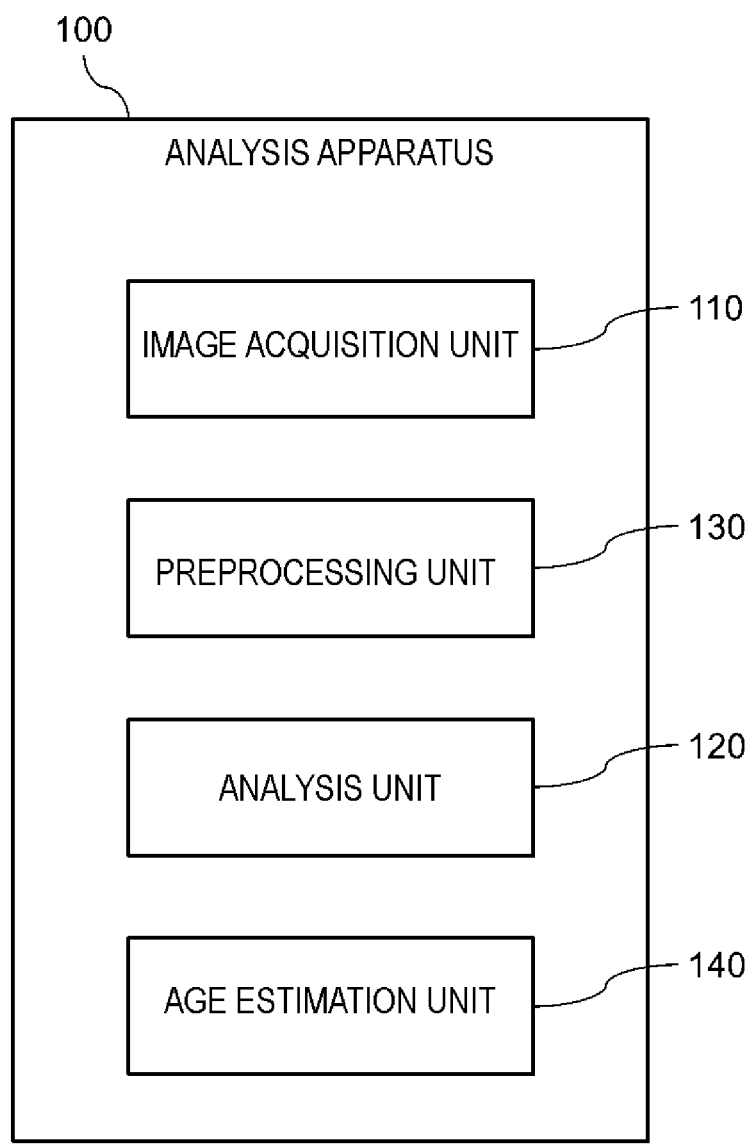
FIG. 4 is a block diagram conceptually showing a functional configuration of an analysis apparatus according to a second example embodiment.

FIG. 4 is a block diagram conceptually showing a functional configuration of an analysis apparatus 100 according to the second example embodiment. As shown in FIG. 4, the analysis apparatus 100 of the present example embodiment has a preprocessing unit 130 and an age estimation unit 140 in addition to the configuration of the first example embodiment. The preprocessing unit 130 executes preprocessing on the image data acquired by the image acquisition unit 110 before the analysis by the analysis unit 120. The age estimation unit 140 estimates and outputs the age of the stratum from which the sample is collected, using the analysis result by an analysis unit.

[Hardware Configuration]

The analysis apparatus 100 of the present example embodiment has the same hardware configuration (for example, FIG. 2) as that of the first example embodiment. The storage device 104 of the present example embodiment further stores program modules implementing functions of the preprocessing unit 130 and the age estimation unit 140 described above, and the processor 102 executes the program modules to realize the functions of the present example embodiment described above.

Operation Example

Figure 5:
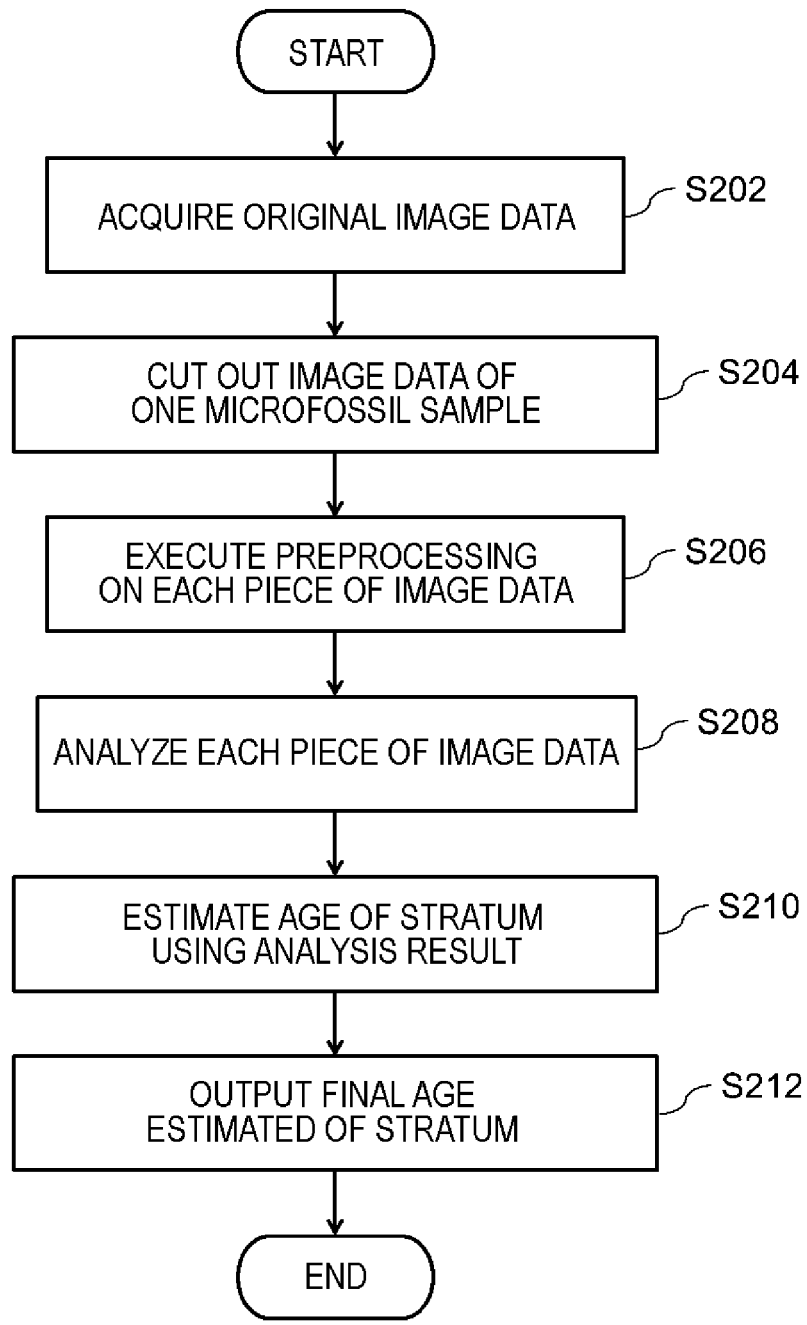
FIG. 5 is a flowchart showing a flow of processing of the analysis apparatus according to the second example embodiment.

An operation example of the analysis apparatus 100 according to the present example embodiment will be described with reference to FIG. 5. FIG. 5 is a flowchart showing a flow of processing of the analysis apparatus 100 according to the second example embodiment.

In the present example embodiment, the image acquisition unit 110 acquires one piece of image data (original image data) generated by imaging a preparation created from the sample collected from the stratum using the microscope apparatus or the like (S202). The original image data is generated by imaging the preparation created for each kind in a to some extent higher class (high-order classification: for example, coccolithophore, diatom, radiolaria, foraminifera, and the like) with the microscope apparatus. The image acquisition unit 110 processes the original image data to cut out a plurality of pieces of image data of one microfossil sample from the original image data (S204). The "image data of one microfossil sample" means image data including one microfossil classified as a kind in a to some extent higher class such as "coccolithophore", "diatom", "radiolaria", and "foraminifera". The image acquisition unit 110 displays the original image data on the monitor 151 and receives an operation input from a user, and thus can decide a cutout region including one microfossil as described above. In addition, the image acquisition unit 110 may be configured to automatically cut out the region including one microfossil as described above from the original image data using a neural network constructed for each kind in a to some extent higher class (higher-order classification: for example, coccolithophore, diatom, radiolaria, foraminifera, and the like). In the present example embodiment, the plurality of pieces of image data cut out by the image acquisition unit 110 are transferred to the preprocessing unit 130 before the analysis by the analysis unit 120.

The preprocessing unit 130 executes the preprocessing on the image data acquired by the image acquisition unit 110 before the analysis by the analysis unit 120 (S206). In order to match the dimension of the data with the training data used in constructing the machine learning result such as the neural network, the preprocessing unit 130 adjusts a resolution (the number of pixels per inch) according to the training data. The preprocessing unit 130 also executes, for example, processing of adjusting at least one of the brightness, the edge, and the contrast of the image data acquired by the image acquisition unit 110.

In this case, the preprocessing unit 130 can acquire information for discriminating the kind of the microfossil to be analyzed together with the image data and execute the preprocessing set for each kind (analysis target) of microfossil discriminated by the information. The information for discriminating the kind of the microfossil is imparted, for example, at the time of generating the original image data or at the time of cutting out the plurality of pieces of image data, and the preprocessing unit 130 can acquire the information for discriminating the kind of the microfossil in the image data together with the image data. In addition, for example, the preprocessing unit 130 may display a screen that receives a user input relating to the information for discriminating the kind of the microfossil on the monitor 151 and acquire the information for discriminating the kind of the microfossil through the screen. The preprocessing unit 130 can perform discrimination on the image data with reference to a table as shown in FIG. 6 on the basis of the information for discriminating the kind of the microfossil.

FIG. 6 is a diagram illustrating information defining preprocessing corresponding to a kind of the microfossil to be analyzed. FIG. 6 illustrates a table in which the information for discriminating the kind of the microfossil to be analyzed and information indicating preprocessing to be executed and an adjustment parameter are stored in association with each other. For example, in a case where "coccolithophore" is obtained as the information for discriminating the kind of the microfossil to be analyzed, the preprocessing unit 130 executes the preprocessing of adjusting "brightness", "edge", and "contrast" using the adjustment parameter. In the example of FIG. 6, only information relating to coccolithophore and diatom is stored. However, the preprocessing of another microfossil (for example, radiolaria and foraminifera) may be further stored.

The preprocessing unit 130 executes the preprocessing on each of the plurality of pieces of image data cut out in the processing of S204 and transfers the plurality of pieces of image data after the processing to the analysis unit 120.

The analysis unit 120 analyzes the plurality of pieces of image data processed by the preprocessing unit 130 to generate the analysis result for each classification (for example, coccolithophore, diatom, radiolaria, foraminifera, and the like) in the previous processing (S208). Here, in order for the image data cut out for each kind, such as coccolithophore, diatom, radiolaria, or foraminifera, in the processing of S204 to be further subdivided in the kind, a machine learning result is further prepared for each kind in a lower class (for example, taxon such as "genus *Pseudoemiliania*" or "genus *Reticulofenestra*" in the case of coccolithophore) for each kind of the microfossils such as coccolithophore, diatom, radiolaria, and foraminifera. Then, the analysis unit 120 generates the analysis result for each taxon using a plurality of machine learning results according to taxa. For example, the analysis unit 120 generates the analysis result as follows.

First, the analysis unit 120 subdivides the classification of the microfossil in the image data using the machine learning result prepared for each kind of the microfossil. The analysis unit 120 may decide which machine learning result may be used, by acquiring the information indicating the kind of the microfossil by an input from the user or on the basis of the information for discriminating the kind of the microfossil in the image data imparted to the image data.

It should be noted that the microfossils may be identical at a classification level such as "coccolithophore" or "diatom" but may have a large difference in an appearance feature (shape) at a lower classification level. The analysis unit 120 may be configured to group the image data classified in the processing of S204 by a classification filter (for example, pattern matching or neural network constructed by learning relating to shape) on the basis of the appearance feature and then analyze the classification using the machine learning result associated with each group.

Then, the analysis unit 120 repeats the processing of inputting the image data classified using a machine learning result of a certain taxon into a machine learning result of a taxon belonging to a class lower than that of the certain taxon to classify the image data and generates an analysis result subdivided to a level where the stratum age can be estimated. The analysis unit 120 generates, as the analysis result, for example, information indicating a taxon of the microfossil in image data and a degree of certainty (certainty factor) for the taxon. The analysis unit 120 can generate the analysis result including the discrimination result of the kind of image data (whether it is "genus *Pseudoemiliania*" or "genus *Reticulofenestra*") and the certainty factor using, for example, the machine learning result for each taxon such as "genus *Pseudoemiliania*" or "genus *Reticulofenestra*" as described above. The analysis unit 120 may further measure a size (for example, diameter or the like) of the microfossil in each piece of image data in order to improve the accuracy of estimating the age. For example, the analysis unit 120 can measure the size of the microfossil in the image data on the basis of the resolution (the number of pixels per inch) of the image data and a pixel region (the number of pixels) of the microfossil and include the measured size in the analysis result. The analysis result generated by the analysis unit 120 is transferred to the age estimation unit 140.

It should be noted that a configuration in which the analysis results are output stepwise from the higher class toward the lower class provides information indicating a process until a final analysis result is obtained. On the basis of the information, it is possible for the user to check how the image data is decided by the machine learning result and perform appropriate measures to improve the analysis accuracy such as tuning (relearning) of the machine learning result or reclassification of the image data by manual or a relearning result.

The age estimation unit 140 estimates the age of the stratum from which the sample is collected, using the analysis result generated by the analysis unit 120 (S210). The age estimation unit 140 first estimates the age of the stratum for each kind of the microfossil using the analysis result obtained for each kind of the microfossil. For example, the age estimation unit 140 can estimate the age of the stratum for each kind of the microfossil as follows.

FIG. 7 is a diagram for illustratively describing a flow in which the age estimation unit 140 estimates the age of the stratum for each kind of the microfossil. (a) of FIG. 7 shows an example of the analysis result acquired by the age estimation unit 140 from the analysis unit 120. Here, a case is illustrated in which seven pieces of image data relating to microfossils classified into four kinds of algae A to D are analyzed by the analysis unit 120, and information indicating the sizes (diameters) of the microfossils in respective pieces of image data and information indicating probabilities that the microfossils are the algae A to D are acquired as the analysis result. The age estimation unit 140 can decide an age estimated for a kind of the microfossil on the basis of the analysis result and a standard distribution of the microfossil for each age. Specifically, the age estimation unit 140 computes a distribution of the microfossil in the sample, as shown in (b) of FIG. 7, on the basis of the analysis result. The age estimation unit 140 may compute the distribution of the microfossil in the sample, for example, from a statistical value such as an average value of the probabilities of the respective analysis results of pieces of image data or may compute the distribution of the microfossil in the sample from a result of determining an alga with the highest probability for each piece of image data as the microfossil in the image data. The age estimation unit 140 compares the computed distribution of the microfossil in the sample with the standard distribution of the fossil for each age as shown in (c) of FIG. 7. It should be noted that a plurality of standard distributions as shown in (c) of FIG. 7 may be prepared in association with area information since a ratio of microfossil assemblages may be influenced by an environmental difference in each area. The age estimation unit 140 receives information indicating a place from which the sample is collected and thus can read out the standard distribution corresponding to the place. The age estimation unit 140 estimates the age of the stratum from which the sample is collected, on the basis of the distribution similarity or the like. In the examples of FIG. 7, in view of the facts that (1) The distributions of algae B to D are closest to age 3, (2) The distribution of alga A is a small amount (5%), and (3) the distribution of alga D is 50%, the age estimation unit 140 may estimate the age of the stratum from which the sample is collected as, for example, "the early period of age 2 to the late period of age 3" or "age 3±X years". It should be noted that the flow described here is merely an example and the present invention is not particularly limited thereto.

For example, the age estimation unit 140 may be configured to process the analysis result using the machine learning result and thus estimate and output the age of the stratum from which the sample is collected. In this case, the machine learning result can be constructed, for example, using training data in which the distribution of the taxon of the microfossil is associated with the estimation result of the age (approximate age and range thereof) corresponding to the distribution.

The age estimation unit 140 estimates a final age on the basis of the age estimated for each kind of the microfossil (S212). For example, the age estimation unit 140 can decide a portion where the age estimated for each kind of the microfossil overlaps as a final estimation result of the age of the stratum from which the sample is collected.

Another Example of Processing of Age Estimation Unit 140

Figure 9:
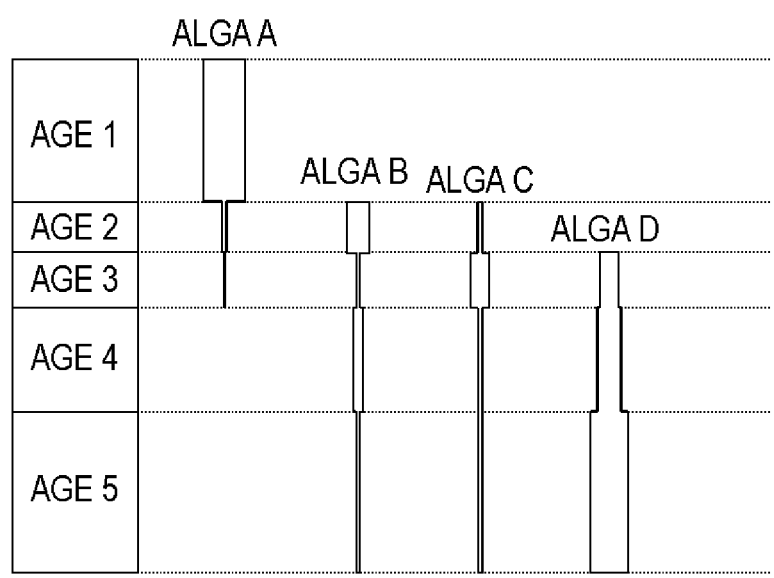
FIG. 9 is a diagram illustrating an existence period of each taxon.

Another example of the processing of the age estimation unit 140 will be described with reference to FIGS. 8 to 10. It should be noted that pieces of processing described below are merely examples and the present invention is not limited to these examples.

First, the age estimation unit 140 acquires the final analysis result of each piece of image data by the analysis unit 120. The analysis result includes information indicating a taxon of the microfossil in each piece of image data and the certainty factor for the taxon (for example, "certainty factor NN % for genus XX of coccolithophore" or the like). The age estimation unit 140 classifies the final analysis result of each piece of image data acquired from the analysis unit 120 into a plurality of stages on the basis of the certainty factor (for example, "certainty factor: high", "certainty factor: medium", and "certainty factor: low") (for example, FIG. 8). FIG. 8 is a diagram showing an example of a result of classifying the final analysis result of each piece of image data on the basis of the certainty factor. For example, a column of "alga A" indicates a result of inputting 100 pieces of image data into the machine learning result of alga A.

Specifically, the column indicates that an analysis result is obtained in which the number of pieces of image data classified into alga A with high certainty factor is 40, the number of pieces of image data classified into alga A with medium certainty factor is 60, and the number of pieces of image data classified into alga A with low certainty factor is zero. The age estimation unit 140 can classify the analysis result of each piece of image data into the plurality of stages on the basis of the certainty factor, using a threshold value, which is common to all taxa or set for each taxon, relating to the certainty factor.

Next, the age estimation unit 140 decides whether or not there is a taxon for which a significant number (for example, 1/10 of the number of pieces of image data) or more of the analysis results classified as "certainty factor: high" are obtained. In a case where the significant number of analysis results classified as "certainty factor: high" are obtained for a certain taxon, the age estimation unit 140 narrows down the age to at least an age corresponding to an existence period of the taxon as a candidate for the age of the stratum from which the sample is collected. For example, assuming that the existence period of each of the algae A to D is defined as shown in FIG. 9, in a case where the analysis result as shown in FIG. 8 is obtained, the age estimation unit 140 narrows down the age to the existence periods (age 1 to age 3) of alga A, for which the significant number of analysis results classified as "certainty factor: high" is obtained, as candidates for the age of the stratum from which the sample is collected. Here, in a case where most analysis results (for example, 80% or more) are classified as "certainty factor: low" for a certain taxon, the age estimation unit 140 may be configured to exclude the age corresponding to the existence period of the taxon from the candidate for the age of the stratum from which the sample is collected. For example, assuming that the existence period of each of the algae A to D is defined as shown in FIG. 9, in the case where the analysis result as shown in FIG. 8 is obtained, the age estimation unit 140 can exclude the existence periods (age 3 to age 5) of alga D from the candidate for the age of the stratum from which the sample is collected.

A plurality of candidates may remain as a result of the above narrowing down. In this case, the age estimation unit 140 computes a score indicating certainty for each of the plurality of candidates on the basis of, for example, the number (percentage) of analysis results classified into "certainty factor: high" and "certainty factor: medium" and thus can output an estimation result of the age on the basis of the score. For example, the age estimation unit 140 determines a taxon for which the significant number or more of analysis results classified as "certainty factor: high" are obtained and assigns a first score (maximum score) to the age corresponding to the existence period of the taxon. The age estimation unit 140 determines a certain taxon for which the number of analysis results classified as "certainty factor: high" is less than the significant number but the number of analysis results of "certainty factor: medium" is equal to or larger than the significant number and assigns a second score smaller than the first score to the age corresponding to the existence period of the taxon. The age estimation unit 140 assigns a third score smaller than the second score to the ages corresponding to the existence periods of taxa other than the above. The age estimation unit 140 computes a statistical value (sum value, average value, or the like) of the score assigned to each age according to the analysis result for each taxon and ranks each of the plurality of candidates narrowed down on the basis of the statistical value. The age estimation unit 140 outputs the plurality of narrowed down candidates in a format in which the ranks can be understood using, for example, a display or a printer. It is possible for the user to select the most likely age on the basis of the output result.

Figure 10:
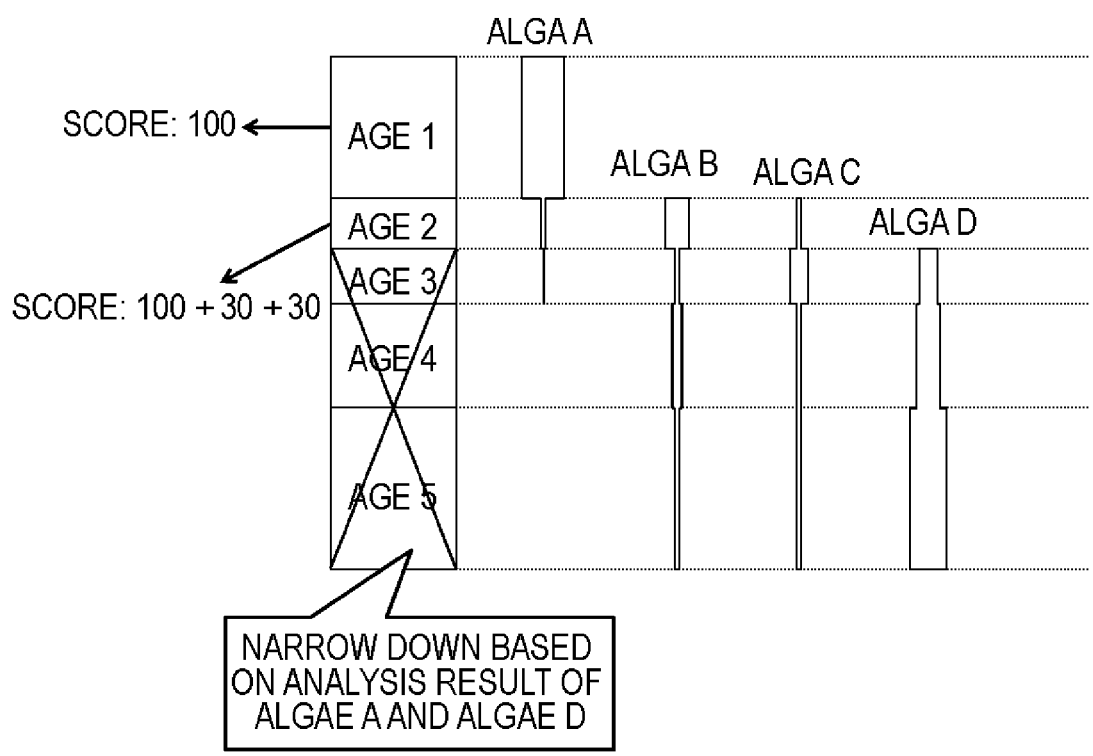
FIG. 10 is a diagram illustrating a flow of another piece of processing of the age estimation unit.

A series of flows are, for example, as shown in FIG. 10. As shown in FIG. 10, the age estimation unit 140 narrows down the candidates to age 1 or age 2 on the basis of the statistics of analysis results of algae A and algae D. The age estimation unit 140 assigns the "first score (for example, "100")" to age 1 corresponding to only the existence period of alga A. The age estimation unit 140 assigns "first score+second score+second score (for example, "100+30+30")" to age 2 corresponding to the existence periods of algae A, B, and C. With the scores, the age estimation unit 140 outputs information indicating that age 2 is the most probable and age 1 is the second most probable as the estimated age of the stratum from which the sample is collected.

As described above, according to the present example embodiment, the result of estimating the age of the stratum is output using the result of analyzing the image data, generated on the basis of the sample collected from the stratum, by the analysis unit 120. As described above, with the analysis apparatus 100 of the present example embodiment, it is possible to automatically estimate the stratum age and thus reduce the load applied to the study of the stratum age.

Modification Example

Figure 11:
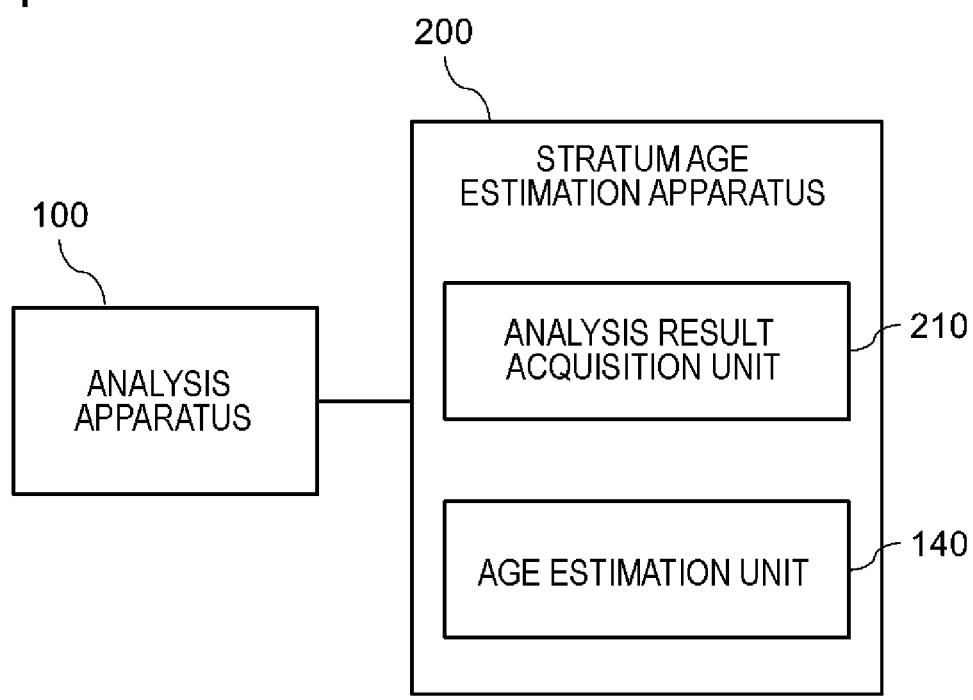
FIG. 11 is a block diagram conceptually illustrating a functional configuration of a modification example according to the second example embodiment.

FIG. 11 is a block diagram conceptually illustrating a functional configuration of a modification example of the second example embodiment. In the present modification example, the age estimation unit 140 described above may be included in an apparatus 200 different from the analysis apparatus 100. The apparatus 200 including the age estimation unit 140 can also be referred to as a "stratum age estimation apparatus". The stratum age estimation apparatus 200 includes an analysis result acquisition unit 210 that acquires an analysis result of a taxon of a microfossil in a sample collected from a stratum in addition to the age estimation unit 140.

In the present modification example, the analysis result acquisition unit 210 can acquire, for example, the information as shown in (a) of FIG. 7 from the analysis apparatus 100. The age estimation unit 140 can decide an age estimated for a kind of the microfossil on the basis of the analysis result and the standard distribution of the microfossil for each age. Specifically, the age estimation unit 140 computes a distribution of the microfossil in the sample on the basis of these analysis results (for example, FIG. (b) of 7) and compares the computed distribution of the microfossil in the sample with the standard distribution of microfossil for each age, and thus can estimate and output the age of the stratum from which the sample is collected. The age estimation unit 140 may be configured to process the analysis result using the machine learning result and thus estimate and output the age of the stratum from which the sample is collected.

[Hardware Configuration]

Figure 12:
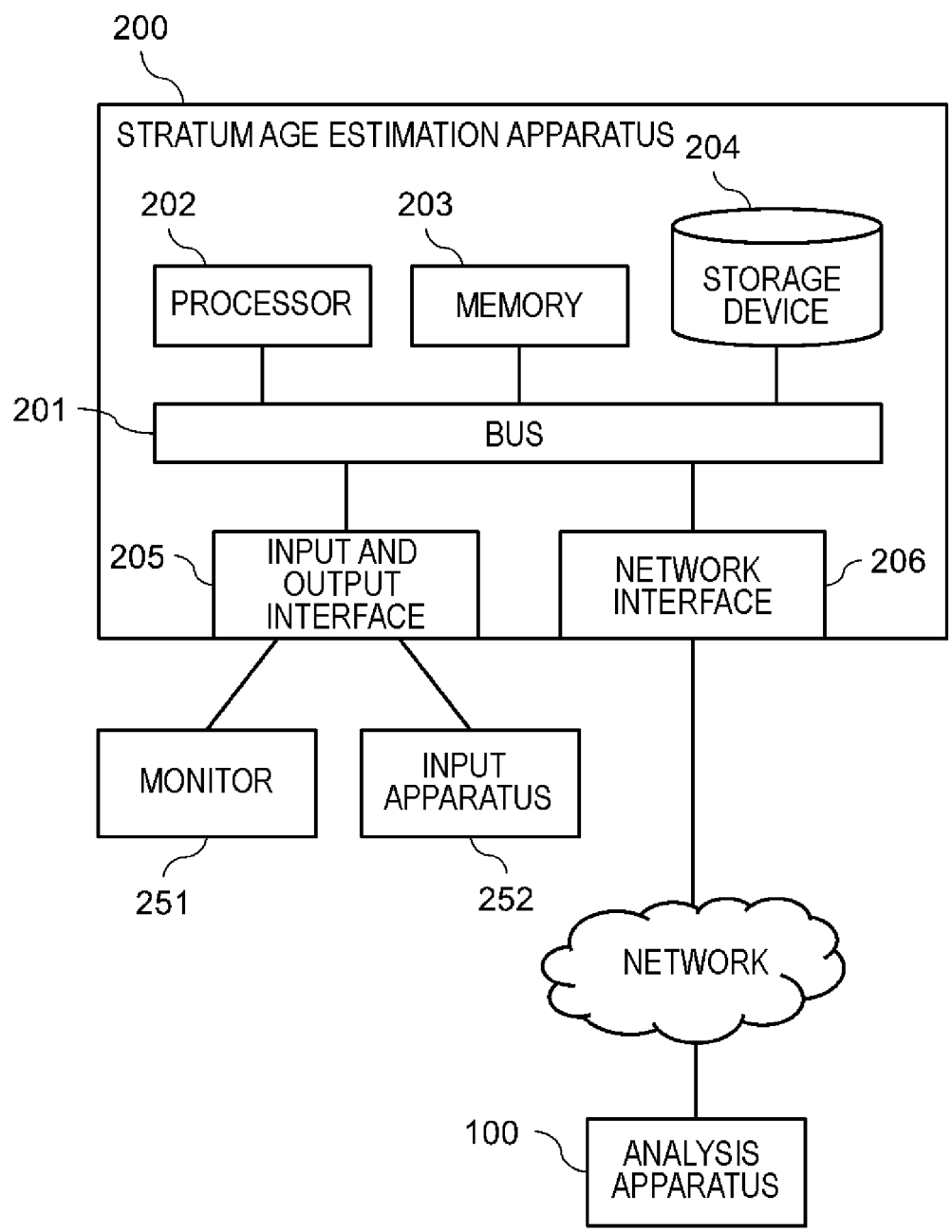
FIG. 12 is a diagram conceptually showing a hardware configuration of a stratum age estimation apparatus.

FIG. 12 is a diagram conceptually showing a hardware configuration of the stratum age estimation apparatus 200. As shown in FIG. 12, the stratum age estimation apparatus 200 is configured to include a bus 201, a processor 202, a memory 203, a storage device 204, an input and output interface 205, and a network interface 206.

The bus 201 is a data transmission path for the processor 202, the memory 203, the storage device 204, the input and output interface 205, and the network interface 206 to mutually transmit and receive data. However, a method of connecting the processor 202, the memory 203, the storage device 204, the input and output interface 205, the network interface 206, and the like to one another is not limited to the bus connection.

The processor 202 is an arithmetic apparatus such as a central processing unit (CPU) or a graphics processing unit (GPU). The memory 203 is a main storage apparatus formed by using a random access memory (RAM), a read only memory (ROM), or the like. The storage device 104 is an auxiliary storage apparatus formed by using a hard disk drive (HDD), a solid state drive (SSD), a memory card, or the like.

The storage device 204 stores program modules implementing the respective functional configuration units (the analysis result acquisition unit 210 and the age estimation unit 140) of the stratum age estimation apparatus 200. The processor 202 reads each of the program modules into the memory 103 and executes each program module to realize a function corresponding to each program module.

The input and output interface 205 is an interface for connecting the stratum age estimation apparatus 200 to a monitor 251, an input apparatus 252, and the like. The input apparatus 252 is a device for input such as a keyboard or a mouse. The monitor 251 is a device for display output such as a liquid crystal display (LCD) or a cathode ray tube (CRT) display.

The network interface 206 is an interface for connecting the stratum age estimation apparatus 200 to a communication network such as a local area network (LAN) or a wide area network (WAN). As shown in FIG. 12, the stratum age estimation apparatus 200 can communicate with the analysis apparatus 100 or an external server apparatus (not shown) by being connected to the communication network through the network interface 206. It should be noted that a method of connecting to the communication network may be a wireless connection or a wired connection.

The example embodiments of the present invention are described with reference to the drawings. However, the example embodiments are examples of the present invention, and various configurations other than the above can be employed.

Figure 13:
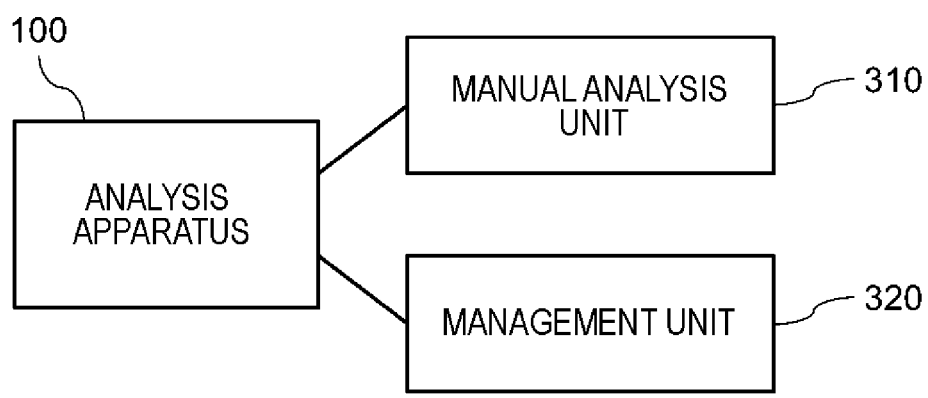
FIG. 13 is a block diagram illustrating another aspect of the present invention.

For example, as shown in FIG. 13, a processing unit that performs a tuning operation for maintaining or improving the accuracy of the machine learning result may be further provided. FIG. 13 is a block diagram illustrating another example embodiment of the present invention. In FIG. 13, a manual analysis unit 310 and a management unit 320 are connected to the analysis apparatus 100.

The management unit 320 is a processing unit that stores various types of data necessary for processing in the manual analysis unit 310 described below. The management unit 320 manages parameters (image adjustment parameter, analysis parameter, parameters relating to age estimation, and the like) used for various computations, the history of machine learning result models, and the like. The management unit 320 sequentially stores operation logs (for example, a set of pieces of input image data of the microfossil and a version of the machine learning result used for classification of the microfossil) in the analysis apparatus 100 such that the manual analysis unit 310 can trace a course until the analysis apparatus 100 outputs a certain result.

The manual analysis unit 310 is a processing unit that manually checks whether the analysis apparatus 100 operates correctly, using information stored in the management unit 320. The manual analysis unit 310 can, for example, check the operation log of the analysis apparatus 100 and perform reclassification processing on the erroneously classified microfossil as a result of using a certain machine learning result model. For example, the manual analysis unit 310 can display the input image data and the classification result (taxon) of the microfossil in the image data on a monitor for a manager, which is not shown, and receive an input for correcting an erroneous classification result. The manual analysis unit 310 also can execute relearning processing with respect to the machine learning result model by which the erroneous classification result is output and can execute the reclassification processing using a machine learning result model on which the relearning processing has been performed. The parameter relating to the age estimation may vary in future studies. For example, as a result of future stratum studies, the existence period of a certain taxon may be shorter or longer than a currently defined period. The manual analysis unit 310 may further include an adjustment function of the parameter relating to the age estimation.

In the plurality of flowcharts used in the above description, the plurality of steps (processing) are described in order. However, the execution order of the steps executed in each example embodiment is not limited to the order of the description. In each example embodiment, the order of the illustrated steps can be changed within the scope of the contents.

Each of the above example embodiments can be combined within the scope in which the contents do not contradict each other.

Some or all of the above example embodiments may be described as in the following additions but are not limited to the additions.

1. An analysis apparatus including: an image acquisition unit that acquires image data of a microfossil in a sample collected from a stratum; and an analysis unit that analyzes the image data using a machine learning result to analyze a taxon or kind of the microfossil in the image data.

2. The analysis apparatus according to 1, in which the analysis unit generates, as an analysis result, information indicating the taxon or kind of the microfossil in the image data and a certainty factor for the taxon or kind.

3. The analysis apparatus according to 1 or 2, in which the image acquisition unit processes one piece of original image data to cut out a plurality of pieces of the image data from the one piece of original image data.

4. The analysis apparatus according to any one of 1 to 3, in which the analysis unit generates an analysis result for each taxon or kind of the microfossil using a plurality of machine learning results prepared for each taxon or kind of the microfossil.

5. The analysis apparatus according to any one of 1 to 4, further including: a preprocessing unit that executes preprocessing on the image data before the analysis by the analysis unit.

6. The analysis apparatus according to 5, in which the preprocessing unit executes processing of adjusting at least one of brightness and an edge of the image data as the preprocessing.

7. The analysis apparatus according to 5 or 6, in which the preprocessing unit acquires information for discriminating an analysis target together with the image data and executes preprocessing decided for each analysis target discriminated by the information.

8. The analysis apparatus according to any one of 1 to 7, further including: an age estimation unit that estimates and outputs an age of the stratum from which the sample is collected, using an analysis result by the analysis unit.

9. The analysis apparatus according to 8, in which the age estimation unit estimates and outputs the age of the stratum from which the sample is collected, using a standard distribution of the microfossil for each age.

10. The analysis apparatus according to 9, in which the age estimation unit computes a distribution of the microfossil in the sample using an analysis result for each taxon or kind of the microfossil by the analysis unit, and estimates and outputs the age of the stratum from which the sample is collected on the basis of the distribution of the microfossil in the sample and the standard distribution of the microfossil for each age.

11. The analysis apparatus according to 8, in which the age estimation unit processes the analysis result using a machine learning result to estimate and output the age of the stratum from which the sample is collected.

12. A stratum age estimation apparatus including: an analysis result acquisition unit that acquires an analysis result of a taxon or kind of a microfossil in a sample collected from a stratum, and an age estimation unit that estimates and outputs an age of the stratum from which the sample is collected, using the analysis result.

13. The stratum age estimation apparatus according to 12, in which the age estimation unit estimates and outputs the age of the stratum from which the sample is collected, using a standard distribution of the microfossil for each age.

14. The stratum age estimation apparatus according to 13, in which the analysis result acquisition unit acquires the analysis result for each taxon or kind of the microfossil in the sample, and the age estimation unit computes a distribution of the microfossil in the sample using the analysis result for each taxon of the microfossil and estimates and outputs the age of the stratum from which the sample is collected on the basis of the distribution of the microfossil in the sample and the standard distribution of the microfossil for each age.

15. The stratum age estimation apparatus according to 12, in which the age estimation unit processes the analysis result using a machine learning result to estimate and output the age of the stratum from which the sample is collected.

16. An analysis method executed by a computer, the method including: acquiring, by the computer, image data of a sample collected from a stratum; and analyzing, by the computer, the image data using a machine learning result to analyze a taxon or kind of a microfossil in the image data.

17. The analysis method according to 16, the method including: generating, by the computer, information indicating the taxon or kind of the microfossil in the image data and a certainty factor for the taxon or kind as an analysis result.

18. The analysis method according to 16 or 17, the method including: processing, by the computer, one piece of original image data to cut out a plurality of pieces of the image data from the one piece of original image data.

19. The analysis method according to any one of 16 to 18, the method including: generating, by the computer, an analysis result for each taxon or kind of the microfossil using a plurality of machine learning results prepared for each taxon or kind of the microfossil.

20. The analysis method according to any one of 16 to 19, the method including: executing, by the computer, preprocessing on the image data before the analysis.

21. The analysis method according to 20, the method including: executing, by the computer, processing of adjusting at least one of brightness and an edge of the image data as the preprocessing.

22. The analysis method according to 20 or 21, the method including: acquiring, by the computer, information for discriminating an analysis target together with the image data and executing, by the computer, preprocessing decided for each analysis target discriminated by the information.

23. The analysis method according to any one of 16 to 22, the method including: estimating and outputting, by the computer, an age of the stratum from which the sample is collected using the analysis result.

24. The analysis method according to 23, the method including: estimating and outputting, by the computer, the age of the stratum from which the sample is collected using a standard distribution of the microfossil for each age.

25. The analysis method according to 24, the method including: computing, by the computer, a distribution of the microfossil in the sample using an analysis result for each taxon or kind of the microfossil; and estimating and outputting, by the computer, the age of the stratum from which the sample is collected on the basis of the distribution of the microfossil in the sample and the standard distribution of the microfossil for each age.

26. The analysis method according to 23, the method including: processing, by the computer, the analysis result using a machine learning result to estimate and output the age of the stratum from which the sample is collected.

27. A stratum age estimation method executed by a computer, the method including: acquiring, by the computer, an analysis result of a taxon or kind of a microfossil in a sample collected from a stratum; and estimating and outputting, by the computer, an age of the stratum from which the sample is collected using the analysis result.

28. The stratum age estimation method according to 27, the method including: estimating and outputting, by the computer, the age of the stratum from which the sample is collected using a standard distribution of the microfossil for each age.

29. The stratum age estimation method according to 28, the method including: acquiring, by the computer, the analysis result for each taxon or kind of the microfossil in the sample; computing, by the computer, a distribution of the microfossil in the sample using the analysis result for each taxon of the microfossil; and estimating and outputting, by the computer, the age of the stratum from which the sample is collected on the basis of the distribution of the microfossil in the sample and the standard distribution of the microfossil for each age.

30. The stratum age estimation method according to 27, the method including: processing, by the computer, the analysis result using a machine learning result to estimate and output the age of the stratum from which the sample is collected.

31. A program causing a computer to function as: an image acquisition unit that acquires image data of a sample collected from a stratum; and an analysis unit that analyzes the image data using a machine learning result to analyze a taxon or kind of a microfossil in the image data.

32. The program according to 31 causing the computer to function as: a unit that generates, as an analysis result, information indicating the taxon or kind of the microfossil in the image data and a certainty factor for the taxon or kind.

33. The program according to 31 or 32 causing the computer to function as: a unit that processes one piece of original image data to cut out a plurality of pieces of the image data from the one piece of original image data.

34. The program according to any one of 31 to 33 causing the computer to function as: a unit that generates an analysis result for each taxon or kind of the microfossil using a plurality of machine learning results prepared for each taxon or kind of the microfossil.

35. The program according to any one of 31 to 34 causing the computer to further function as: a preprocessing unit that executes preprocessing on the image data before the analysis by the analysis unit.

36. The program according to 35 causing the computer to function as: a unit that executes processing of adjusting at least one of brightness and an edge of the image data as the preprocessing.

37. The program according to 35 or 36 causing the computer to function as: a unit that acquires information for discriminating an analysis target together with the image data and executes preprocessing decided for each analysis target discriminated by the information.

38. The program according to any one of 31 to 37 causing the computer to further function as: an age estimation unit that estimates and outputs an age of the stratum from which the sample is collected, using an analysis result by the analysis unit.

39. The program according to 38 causing the computer to function as: a unit that estimates and outputs the age of the stratum from which the sample is collected, using a standard distribution of the microfossil for each age.

40. The program according to 39 causing the computer to function as: a unit that computes a distribution of the microfossil in the sample using an analysis result for each taxon or kind of the microfossil by the analysis unit, and estimates and outputs the age of the stratum from which the sample is collected on the basis of the distribution of the microfossil in the sample and the standard distribution of the microfossil for each age.

41. The program according to 38 causing the computer to function as: a unit that processes the analysis result using a machine learning result to estimate and output the age of the stratum from which the sample is collected.

42. A program causing a computer to function as: an analysis result acquisition unit that acquires an analysis result of a taxon or kind of a microfossil in a sample collected from a stratum, and an age estimation unit that estimates and outputs an age of the stratum of the sample, using the analysis result.

43. The program according to 42 causing the computer to function as: a unit that estimates and outputs the age of the stratum from which the sample is collected, using a standard distribution of the microfossil for each age.

44. The program according to 43 causing the computer to function as: a unit that acquires the analysis result for each taxon or kind of the microfossil in the sample, computes a distribution of the microfossil in the sample using the analysis result for each taxon of the microfossil, and estimates and outputs the age of the stratum from which the sample is collected on the basis of the distribution of the microfossil in the sample and the standard distribution of the microfossil for each age.

45. The program according to 42 causing the computer to function as: a unit that processes the analysis result using a machine learning result to estimate and output the age of the stratum from which the sample is collected.

This application claims priority on the basis of Japanese Patent Application No. 2017-094086, filed May 10, 2017, the entire disclosure of which is incorporated herein.

The invention claimed is:
1. An analysis apparatus comprising:
at least one memory configured to store instructions; and
at least one processor configured to execute the instructions to perform operations comprising:
acquiring image data of a microfossil in a sample collected from a stratum and identification information for identifying a type of microfossil to be analyzed;
determining, based on the type of microfossil identified by the identification information, preprocessing to be performed on the image data;
performing the preprocessing on the image data to generate processed image data; and
inputting the preprocessed image data to a machine learning result to output information on a taxon or kind of the microfossil in the image data.
2. The analysis apparatus according to claim 1,
wherein the operations further comprise generating, as an analysis result, information indicating the taxon or kind of the microfossil in the image data and a certainty factor for the taxon or kind.

3. The analysis apparatus according to claim 1, wherein the operations further comprise processing one piece of original image data to cut out a plurality of pieces of the image data from the one piece of original image data.

4. The analysis apparatus according to claim 1, wherein the operations further comprise generating an analysis result for each taxon or kind of the microfossil using a plurality of machine learning results prepared for each taxon or kind of the microfossil.

5. The analysis apparatus according to claim 1, wherein the operations further comprise executing processing of adjusting at least one of brightness and an edge of the image data as the preprocessing.

6. The analysis apparatus according to claim 1, wherein the operations further comprise estimating and outputting an age of the stratum from which the sample is collected, using an analysis result of the processed image data.

7. The analysis apparatus according to claim 6, wherein the operations further comprise estimating and outputting the age of the stratum from which the sample is collected, using a standard distribution of the microfossil for each age.

8. The analysis apparatus according to claim 7, wherein the operations further comprise:
computing a distribution of the microfossil in the sample using an analysis result for each taxon or kind of the microfossil; and
estimating and outputting the age of the stratum from which the sample is collected on the basis of the distribution of the microfossil in the sample and the standard distribution of the microfossil for each age.

9. The analysis apparatus according to claim 6, wherein the operations further comprise processing the analysis result using a machine learning result to estimate and output the age of the stratum from which the sample is collected.

10. An analysis method executed by a computer, the method comprising:
acquiring image data of a microfossil in a sample collected from a stratum and identification information for identifying a type of microfossil to be analyzed;
determining, based on the type of microfossil identified by the identification information, preprocessing to be performed on the image data;
performing the preprocessing on the image data to generate processed image data; and
inputting the processed image data to a machine learning result to output information on a taxon or kind of a microfossil in the image data.

11. A non-transitory computer readable medium storing a program causing a computer to execute a method, the method comprising:
acquiring image data of a microfossil in a sample collected from a stratum and identification information for identifying a type of microfossil to be analyzed;
determining, based on the type of microfossil identified by the identification information, preprocessing to be performed on the image data;
performing the preprocessing on the image data to generate processed image data; and
inputting the processed image data to a machine learning result to output information on a taxon or kind of a microfossil in the image data.

* * * * *